United States Patent [19]

Harbridge

[11] Patent Number: 4,584,291
[45] Date of Patent: Apr. 22, 1986

[54] 9-DEOXY-9-TETRAZOLYL-DERIVATIVES OF CLAVULANIC ACID, THEIR PREPARATION AND THEIR USE

[75] Inventor: John B. Harbridge, Coulsdon, England

[73] Assignee: Beecham Group p.l.c., England

[21] Appl. No.: 590,415

[22] Filed: Mar. 16, 1984

Related U.S. Application Data

[63] Continuation of Ser. No. 325,979, Nov. 30, 1981, abandoned.

[30] Foreign Application Priority Data

Dec. 9, 1980 [GB] United Kingdom ............... 8039447
Jun. 12, 1981 [GB] United Kingdom ............... 8118110

[51] Int. Cl.⁴ .................. C07D 498/04; A61K 31/42; A61K 31/445
[52] U.S. Cl. .................................. 514/210; 546/270; 260/245.3
[58] Field of Search ............ 424/272; 260/245.3; 546/198, 270; 514/210

[56] References Cited

U.S. PATENT DOCUMENTS

| | | | |
|---|---|---|---|
| 4,093,626 | 6/1978 | Hunt | 260/245.3 |
| 4,315,006 | 2/1982 | Storer | 424/250 |
| 4,315,935 | 2/1982 | Ali | 424/258 |
| 4,316,907 | 2/1982 | Oxford et al. | 549/60 |
| 4,317,826 | 3/1982 | Gleason | 424/258 |
| 4,317,835 | 3/1982 | Van Dijk et al. | 424/300 |
| 4,321,254 | 3/1982 | Ali | 424/40 |
| 4,341,786 | 7/1982 | Demarinis et al. | 424/258 |
| 4,350,685 | 9/1982 | Ali et al. | 424/45 |
| 4,351,842 | 9/1982 | Coles | 424/274 |
| 4,352,809 | 10/1982 | Bondinell et al. | 424/258 |
| 4,366,167 | 12/1982 | Corbett | 424/274 |
| 4,379,787 | 4/1983 | Lunn et al. | 424/246 |
| 4,382,084 | 5/1983 | Ponsford et al. | 424/114 |
| 4,382,932 | 5/1983 | Lunn et al. | 424/246 |
| 4,385,047 | 5/1983 | Ali | 424/43 |
| 4,388,316 | 6/1983 | Lunn et al. | 424/246 |
| 4,393,072 | 7/1983 | Merkel et al. | 424/275 |
| 4,395,406 | 7/1983 | Gacek et al. | 424/180 |
| 4,395,421 | 7/1983 | Taylor et al. | 424/283 |
| 4,396,619 | 8/1983 | Lunn et al. | 424/246 |
| 4,396,620 | 8/1983 | Lunn | 424/246 |
| 4,397,845 | 8/1983 | Allen | 424/180 |
| 4,399,142 | 8/1983 | Durant et al. | 424/258 |
| 4,401,665 | 8/1983 | Sheinaus et al. | 424/233 |
| 4,401,668 | 8/1983 | Lunn | 424/246 |
| 4,402,949 | 9/1983 | Hartmann et al. | 424/183 |
| 4,402,955 | 9/1983 | Lunn | 424/246 |
| 4,402,974 | 9/1983 | Matier et al. | 424/308 |
| 4,402,976 | 9/1983 | Muir | 424/311 |
| 4,405,596 | 9/1983 | Helbig et al. | 424/33 |
| 4,406,898 | 9/1983 | Lunn et al. | 424/246 |
| 4,406,899 | 9/1983 | Aburaki et al. | 424/246 |
| 4,411,907 | 10/1983 | Toia | 424/273 B |
| 4,411,909 | 10/1983 | Gonella | 424/275 |
| 4,414,204 | 11/1983 | Tarcsay et al. | 424/177 |
| 4,421,760 | 12/1983 | Box | 424/274 |
| 4,427,690 | 1/1984 | Cole et al. | 424/272 |
| 4,428,958 | 1/1984 | Ponsford | 424/272 |
| 4,444,754 | 4/1984 | Stirling et al. | 424/114 |
| 4,444,783 | 4/1984 | Eglington | 424/114 |
| 4,446,146 | 5/1984 | Southgate et al. | 424/274 |

OTHER PUBLICATIONS

Merck Index, Ninth Edition, pp. 7554, 7556, 7557, 9036.
Newall et al, Chem. Abs., 93, 22497a (1979).
Newall et al, Chem. Ab., 95, 97651k (1980).

Primary Examiner—Mark L. Berch
Attorney, Agent, or Firm—Jacobs & Jacobs

[57] ABSTRACT

Tetrazolyl derivatives of clavulanic acid are described, having the formula:

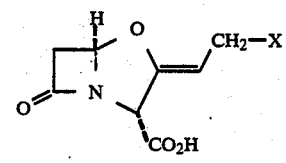

wherein X is an optionally substituted tetrazolyl group attached via a nitrogen atom. These compounds are useful as antibiotics and β-lactamase inhibitors.

19 Claims, No Drawings

9-DEOXY-9-TETRAZOLYL-DERIVATIVES OF CLAVULANIC ACID, THEIR PREPARATION AND THEIR USE

This is a continuation of Ser. No. 325,979, filed Nov. 30, 1981, now abandoned.

This invention relates to derivatives of clavulanic acid and in particular to 9-N-tetrazolyldeoxyclavulanate derivatives. These are of use as antibiotics and as β-lactamase inhibitors.

Clavulanic acid and salts and esters thereof are described in U.K. Pat. No. 1,508,977; clavulanic acid has the formula (I):

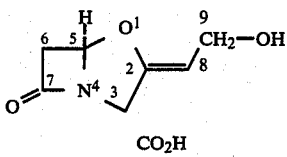

The present invention relates to compounds wherein the hydroxy group at C-9 position is replaced by a tetrazole group.

Accordingly the present invention provides a compound of formula (II) or a salt or ester thereof:

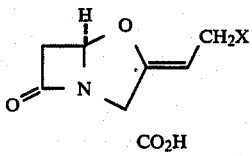

wherein X is an optionally substituted tetrazolyl group attached via a nitrogen atom.

Suitably X represents a group of sub-formula (i):

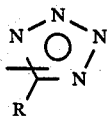

wherein R is hydrogen; esterified or salified carboxy, optionally substituted $C_{1-6}$alkoxy, $C_{1-6}$alkyl, $C_{2-6}$alkenyl, or aryl; azido, isocyano, cyano, nitro, bromo, chloro, or is a group of the sub-formula (a):

$$-(CO)_n-NR^1R^2 \qquad (a)$$

wherein n is zero or one; $R^1$ is hydrogen or optionally substituted $C_{1-6}$alkyl, $C_{1-6}$alkanoyl, or arylcarbonyl; and $R^2$ is hydrogen, $C_{1-6}$alkyl or $C_{1-6}$alkanoyl; or $R^1$ and $R^2$ may be joined to form with the nitrogen atom to which they are attached, an optionally substituted 4, 5 or 6-membered ring.

In one aspect suitably X represents a group of sub-formula (i):

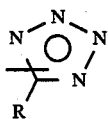

wherein R is hydrogen; optionally substituted $C_{1-6}$alkoxy, $C_{1-6}$alkyl, $C_{2-6}$alkenyl, or aryl; azido, isocyano, cyano, nitro, bromo, chloro, or is a group of the sub-formula (aa):

$$-NR^1R^2 \qquad (aa)$$

wherein $R^1$ is hydrogen or optionally substituted $C_{1-6}$alkyl, $C_{1-6}$alkanoyl, or arylcarbonyl; and $R^2$ is hydrogen, $C_{1-6}$alkyl or $C_{1-6}$alkanoyl; or $R^1$ and $R^2$ may be joined to form with the nitrogen atom to which they are attached, an optionally substituted 4, 5 or 6-membered ring.

The compounds of the formula (II) may be presented in the form of the carboxylic acid at the C-3 position. Alternatively the compounds of the formula (II) may be in the form of a pharmaceutically acceptable salt. Suitable pharmaceutically acceptable salts of the compounds of formula (II) include metal salts, for example aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or with procaine, dibenzylamine, N,N-dibenzylethylenediamine, 1-ephenamine, N-ethylpiperidine, N-benzyl-β-phenethylamine, dehydroabietylamine or N,N-bisdehydroabietylamine.

Compounds of the formula (II) when in the form of nonpharmaceutically acceptable salts, for example the lithium salt or the silver salt are also of use for example as intermediates in preparing pharmaceutically acceptable salts.

The compounds of the formula (II) alternatively may be provided as in vivo hydrolysable esters. Such esters are those which hydrolyse in the human body to produce the parent acid or salt thereof. Suitable in vivo hydrolysable esters include those of the sub-formulae (b) and (c):

$$-CO-O-CHR^3-O-CO-R^4 \qquad (b)$$

$$-CO-O-R^5-NR^6R^7 \qquad (c)$$

wherein $R^3$ is hydrogen atom or a methyl or phenyl group; $R^4$ is $C_{1-6}$alkyl, phenyl, phenyl $(C_{1-3})$alkyl, $C_{1-6}$alkoxy, phenoxy, phenyl $(C_{1-3})$alkoxy; or $R^3$ and $R^4$ are joined to form a 1,2-diphenylene or 4,5-dimethoxy-1,2-diphenylene group: $R^5$ is a divalent methylene or ethylene radical, $R^6$ and $R^7$ are independently methyl or ethyl groups.

Favourably $R^3$ is a hydrogen atom.

When $R^3$ is a hydrogen atom suitably $R^4$ is selected from methyl, ethyl, n-propyl, isopropyl, n-butyl, tert-butyl, phenyl, benzyl, methoxy, ethoxy, n-propyloxy and isopropyloxy. Preferably $R^4$ is tert-butyl.

Favourably $R^3$ and $R^4$ are joined so that the ester is a phthalidyl or 3,4-dimethoxyphthalidyl ester.

Of these, the preferred esters are the acetoxymethyl, α-ethoxycarbonyloxyethyl, pivaloyloxymethyl and phthalidyl esters, of which the phthalidyl is favoured.

The in vivo hydrolysable nature of the ester may be confirmed by administration to an animal such as a mouse or rat and determination of the presence of a compound of the formula (II) or salt thereof in the body fluids of the animal, for example the blood or urine. Alternatively hydrolysis in human blood or serum may be determined.

Suitably group R may be optionally substituted by one or more groups or atoms selected from hydroxy, halo, aryl, carboxy, $C_{1-6}$alkanoyl, $C_{1-6}$alkanoyloxy, $C_{1-6}$alkoxy, $C_{1-6}$alkoxycarbonyl, aryl ($C_{1-6}$) alkoxy, arylcarbonyl, $C_{1-6}$alkylthio, arylthio, amino, azido, $C_{1-6}$alkylamino or di($C_{1-6}$)alkylamino.

Suitably $R^1$ when it is not methyl may optionally be substituted by one or more groups selected from hydroxy, halo, carboxy, $C_{1-6}$alkanoyl, $C_{1-6}$alkanoyloxy, $C_{1-6}$alkoxy, $C_{1-6}$alkoxycarbonyl, $C_{1-10}$aralkoxy, arylcarbonyl, $C_{1-6}$alkylthio, arylthio, amino, $C_{1-6}$alkylamino or di($C_{1-6}$)alkylamino.

Suitably $R^2$ when it is not methyl may optionally be substituted by one or more groups selected from hydroxy, halo, carboxy, $C_{1-6}$alkanoyl, $C_{1-6}$alkanoyloxy, $C_{1-6}$alkoxy, $C_{1-6}$alkoxycarbonyl, aryl ($C_{1-6}$) alkoxy, arylcarbonyl, $C_{1-6}$alkylthio, arylthio, amino, $C_{1-6}$alkylamino or di($C_{1-6}$)alkylamino.

When $R^1$ is methyl suitably it may optionally be substituted by carboxy, $C_{1-6}$alkanoyl, $C_{1-6}$alkanoyloxy, $C_{1-6}$alkoxycarbonyl or arylcarbonyl.

When $R^2$ is methyl suitably it may optionally be substituted by carboxy, $C_{1-6}$alkanoyl, $C_{1-6}$alkanoyloxy, $C_{1-6}$alkoxycarbonyl or arylcarbonyl.

When used herein the term "aryl" includes phenyl, pyrrolyl, furyl, thienyl, indolyl, benzofuryl, thianaphthyl, and any of such groups being optionally substituted.

Suitably R is a hydrogen atom. Suitably also R is a $C_{1-6}$alkyl, $C_{2-6}$alkenyl, $C_{1-10}$aralkyl or aryl group, any of such groups being optionally substituted. More suitably R is methyl, ethyl, t-butyl, phenyl, benzyl or carboxymethyl.

Suitably when R is salified carboxy, the carboxy group is salified with a pharmaceutically acceptable salt, suitable salts being as described in relation to the C-3 carboxy. Suitably when R is esterified carboxy the esterifying group is an in vivo hydrolysable ester of sub-formula (b) or (c) as hereinbefore defined, or alternatively an ester of the sub-formulae (d) or (e):

CO—$OA^1$                                         (d)

CO—O—$CHA^2A^3$                        (e)

wherein $A^1$ is $C_{1-6}$alkyl optionally substituted by $C_{1-7}$alkoxy; $A^2$ is $C_{2-5}$alkenyl optionally substituted by phenyl or is a phenyl group optionally substituted by one or more atoms or groups selected from fluorine, chlorine, bromine, nitro, $C_{1-4}$alkyl or $C_{1-4}$alkoxy; and $A^3$ is hydrogen, $C_{1-4}$alkyl or a phenyl group optionally substituted by fluorine, chlorine, bromine, nitro, $C_{1-4}$alkyl or $C_{1-4}$alkoxy. Most suitably $A^1$ is a $C_{1-6}$alkyl group such as methyl or propyl; or $CHA^2A^3$ is a benzyl or substituted benzyl group.

Suitably R is a group of the sub-formula —$CONR^1R^2$ as hereinbefore defined. More suitably $R^1$ is a hydrogen atom or optionally substituted $C_{1-6}$alkyl group. More suitably $R^2$ is a hydrogen atom.

Suitably R is a group of sub-formula —$NR^1R^2$ as hereinbefore defined. Most suitably $R^1$ is a hydrogen atom, $C_{1-6}$alkyl, $C_{1-6}$alkanoyl or $C_{1-10}$aralkanoyl, any of such groups being optionally substituted. More suitably $R^2$ is a hydrogen atom. Favourably when $R^2$ is a hydrogen atom $R^1$ is a hydrogen atom or a $C_{1-6}$alkanoyl group such as acetyl.

This invention extends to the compounds of the formula (II) in both the structural forms (III) and (IV):

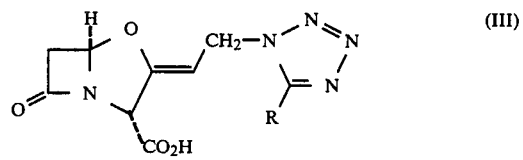

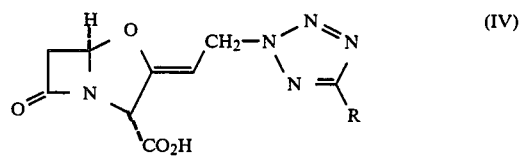

That is the C-9 substituent is either a tetrazol-1-yl or tetrazol-2-yl group.

The present invention also provides a pharmaceutical composition which comprises a compound of the formula (II) or a pharmaceutically acceptable salt or in vivo hydrolysable ester thereof and a pharmaceutically acceptable carrier.

The compositions of the invention include those in a form adapted for oral, topical or parenteral use and may be used for the treatment of the infection in animals, particularly in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form.

The injectable solution of the compound of this invention may be made up in a sterile pyrogen-free liquid such as water, aqueous ethanol or the like.

An alternative approach to administering the compounds of this invention is to utilise an injectable suspension. Such suspensions may be made up in sterile water; sterile saline or the like and may also contain suspending agents such as polyvinylpyrrolidone, lecithin or the like Alternatively such compositions may be prepared in an acceptable oil suspending agent such as arachis oil or its equivalent. For use in such suspensions the compounds of this invention should be in the form of fine particles.

Unit dose compositions comprising a compound of this invention adapted for oral administration form a further suitable composition aspect of this invention.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin which shows instability to β-lactamases since the resulting composition shows enhanced effectiveness (synergy). Suitable penicillins cephalosporins or other β-lactam antibiotic for inclusion in such synergistic compositions include not only those known to be highly susceptible to β-lactamases but also those which have a degree of intrinsic resistance to β-lactamases.

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, sulbenicillin, piperacillin, and other known penicillins including pro-drugs therefor such as their in vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde or ketone adducts of penicillins containing a 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole nafate, cephapirin, cephradine, 4-hydroxycephaloexin, cefaparole, cephaloglycin, cefoperazone, and other known cephalosporins or prodrugs therefor.

Such compounds are frequently used in the form of a salt or hydrate of the like.

Naturally if the penicillin or cephalosporin present in the composition is not suitable for oral administration then the composition will be adapted for parenteral administration.

Highly favoured penicillins for use in the compositions of this invention include ampicillin, amoxycillin, carbenicillin and ticarcillin. Such penicillins may be used as a pharmaceutically acceptable salt such as the sodium salt. Alternatively he ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin which may be in the form of a pharmaceutically acceptable salt for example the sodium salt.

When present together with a cephalosporin or penicillin, the ratio of a compound of the invention to the penicillin or cephalosporin agent may vary over a wide range of ratios, such as from 10:1 to 1:15 for example 10:1 to 1:10 such as about 3:1, 2:1, 1:1, 1:2, 1:3, 1:4, 1:5 or 1:6 (wt/wt, based on pure free antibiotic equivalent).

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 3000 mg of the compounds of the invention will be administered each day of treatment but more usually between 100 and 1000 mg of the compounds of the invention will be administered per day, for example at 1–6 doses, more usually as 2, 3 or 4 doses. However for the treatment of more severe systemic infections or infections of particularly intransigent organisms higher doses may be used in accordance with clinical practice.

The penicillin or cephalosporin in the synergistic composition of this invention will normally be present at approximately the amount at which it is conventionally used which will usually be expected to be from about 62.5 to 3000 mg per dose, more usually about 125, 250, 500 or 1000 mg per dose.

One particularly favoured composition of this invention will contain from 150 to 1000 mg of amoxycillin as the trihydrate or sodium salt and from 25 to 500 mg of a compound of this invention.

A further particularly favoured composition of this invention will contain from 150 to 1000 mg of ampicillin or a pro-drug therefor and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitable this form of the composition will contain a compound of the formula (II) when in crystalline form.

Most suitably the preceding composition will contain from 200 to 700 mg of the penicillin component. Most suitably the preceding composition will comprise from 50 to 250 mg of a compound of the formula (II) preferably in crystalline form.

Such compositions may be adapted for oral or parenteral use except when containing an in vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefor and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formula (II) preferably in crystalline form. Such compositions containing di-salts of carbenicillin and ticarcillin will be adapted for parenteral administration.

The present invention also provides a method of treating bacterial infections in animals, particularly humans or domestic mammals, which comprises the administration of a composition of this invention.

Commonly the infection treated will be due to a strain of *Staphylococcus aureus, Klebsiella aerogenes, Escherichia coli, Proteus sp., Bacteroides fragilis* or the like. The organisms believed to be most readily treated by an antibacterially effective amount of a compound of this invention is *Staphylococcus aureus*. The other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

In another aspect the present invention provides a process for the preparation of a compound of the formula (II) or a salt or ester thereof which process comprises the reaction of a compound of the formula (V):

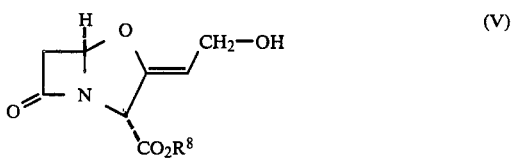

wherein $R^8$ is an esterifying group, with:
(i) a compound of the formula (VI):

$$H-X \qquad (VI)$$

wherein X is as defined in relation to formula (II), and is attached via a nitrogen atom to the hydrogen atom:
(ii) a stabilised diazoalkane, or a compound of formula (VII):

$$R^9OCON=NCOOR^{10} \qquad (VII)$$

wherein $R^9$ and $R^{10}$ are independently $C_{1-6}$alkyl, aryl or aryl ($C_{1-6}$)alkyl; and
(iii) a compound of the formula (VIII):

wherein l, m and n are independently 0 or 1 and $R^{11}$, $R^{12}$ and $R^{13}$ are each independently $C_{1-6}$alkyl, aryl ($C_{1-6}$)alkyl or aryl; and thereafter if desired:
(iv) converting any ester group into a carboxylic acid or salt;
(V) converting a carboxylic acid or salt into an in vivo hydrolysable ester.
(vi) converting a compound of the formula (II) wherein R is esterified or salified carboxy into a compound of the formula (II) wherein R is hydrogen.

Sutiably compounds of the formula (VI) are of the sub-formula (VIa):

wherin R is as defined in relation to formula (II).

Suitable compounds of the formula (VII) include those wherein $R^9$ and $R^{10}$ are independently selected from methyl, ethyl, propyl, butyl, phenyl and benzyl groups. It is generally convenient that $R^9$ and $R^{10}$ represent the same moiety. Particularly suitable compounds of the formula (VII) include those wherein $R^9$ and $R^{10}$ each represent a methyl, ethyl, t-butyl or iso-propyl group.

Alternatively the compound of the formula (VII) may be replaced by a stabilised diazoalkane, such as diphenyldiazomethane or ethyl diazoacetate. This aspect is not preferred when the compound of the formula (VI) is strongly acidic.

Suitable compounds of the formula (VIII) include those wherein the $R^{11}$, $R^{12}$ and $R^{13}$ groups are selected from methyl, ethyl, n-propyl, n-butyl, benzyl, phenyl and methoxyphenyl groups. It is generally convenient that $R^{11}$, $R^{12}$ and $R^{13}$ each represent the same moiety. Favoured compounds of the formula (VIII) include tri-arylphosphines and tri-alkylphosphites. Particularly suitable compounds of the formula (VIII) include triphenylphosphine, trimethylphosphite, tri-ethylphosphite, tri-p-methoxyphenylphosphine and tri-n-butylphosphine.

Any convenient ester of clavulanic acid may be used in this reaction (ie the compound of the formula (V) but in general it is most suitable to use an in-vivo hydrolysable ester of sub-formulae (b) or (c) as hereinbefore defined, or alternatively an ester of sub-formulae (d) or (e) may be used as such esters are readily converted to the parent acid or its salt by methods appropriate to the particular ester, for example basic hydrolysis, enzymatically-catalysed hydrolysis hydrogenolysis, electrolysisor photolysis.

$$CO-O-A^1 \qquad (d)$$

$$CO-O-CHA^2A^3 \qquad (e)$$

wherein $A^1$ is $C_{1-6}$alkyl optionally substituted by $C_{1-7}$alkoxy; $A^2$ is $C_{2-5}$alkenyl optionally substituted by phenyl or is a phenyl group optionally substituted by one or more atoms or groups selected from fluorine, chlorine, bromine, nitro, $C_{1-4}$alkyl or $C_{1-4}$alkoxy; and $A^3$ is hydrogen, $C_{1-4}$alkyl or a phenyl group optionally substituted by fluorine, chlorine, bromine, nitro, $C_{1-4}$alkyl or $C_{1-4}$alkoxy.

Further suitable ester-forming groups are those which may also be removed under conventional conditions by methods appropriate to the particular ester, for example basic hydrolysis, enzymatically-catalysed hydrolysis or hydrogenolysis, for example benzoylmethyl, pyridylmethyl, 2,2,2-trichloroethyl, 2,2,2-tribromoethyl, triphenylmethyl, 2-benzyloxyphenyl, 4-methoxycarbonylbenzyl, 4-methylthiophenyl, or a silyl, stannyl or pentavalent phosphorus-containing group.

Particularly suitable esters of clavulanic acid for use in this process include methoxymethyl clavulanate, benzyl clavulanate, p-nitrobenzyl clavulanate, p-methoxybenzyl clavulanate, methyl clavulanate, and silyl esters such as tri-($C_{1-6}$)alkylsilyl clavulanates and di-($C_{1-6}$)alkyl-phenyl silyl clavulanates, for example tri-isopropylsilyl clavulanate and di-tert-butyl-phenyl silyl clavulanate.

In general it has been found suitable to use one more of an ester of clavulanic acid, a slight molar excess of both of the compounds of the formulae (VII) and (VIII), and two molar equivalents of the tetrazole of the formula (VI).

The reaction is performed in an inert organic solvent. The solvent used should be aprotic and substantially unreactive towards the reagents involved. Suitable solvents include tetrahydrofuran, dioxan, ethyl acetate, benzene, toluene and chlorobenzene. Of these tetrahydrofuran is preferred. On occasion it is necessary to have a small proportion of dimethylformamide in the reaction solvent to aid solubility of the compound of the formula (VI).

The reaction is normally carried out at a nonextreme temperature such as −20° C. to +100° C., more usually from about 5° C. to 50° C. and conveniently at ambient temperature (approximately 15° C. to 25° C.).

Once the reaction is complete de-esterfication may be performed in conventional manner to afford the carboxylic acid or salt thereof. The lithium salts of the compounds of the formula (II) may be formed first and then converted to a different salt, for example by ion-exchange. The salts and free acids of the compounds of the formula (II) may be converted to esters of the compounds of the formula (II) in conventional manner, for example by reaction with one equivalent of a reactive halide in a solvent such as dimethylformamide.

The foregoing process provides the compounds of the formula (II) and salts and esters thereof when in structural formula (III) or (IV).

A compound of the formula (II) wherein R is esterified carboxy may be converted into a compound of the formula (II) wherein R is salified carboxy in conventional manner, for example, the methods for de-esterification of the C-3 ester of clavulanic acid may be used where appropriate, in particular basic hydrolysis of alkyl esters is useful. Conversion of a compound of the formula (II) wherein R is salified carboxy to a compound of the formula (II) wherein R is hydrogen may be in conventional manner for example by acidification, extraction into organic solvent and treatment with aqueous base.

In another aspect the present invention provides a process for the preparation of a compound of the formula (III) or salt or ester thereof which process comprises the reaction of azide ion with an ester of a compound of the formula (IX):

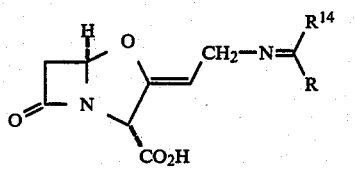

wherein R is as defined in relation to formula (II) and $R^{14}$ is a bromine or chlorine atom, and thereafter if desired:
  (i) converting any ester group into a carboxylic acid or salt;
  (ii) converting a carboxylic acid or salt into an in vivo hydrolysable ester.
  (iii) converting a compound of the formula (III) wherein R is esterified or salified carboxy into a compound of the formula (III) wherein R is hydrogen.

The reaction is suitably performed in an inert organic solvent such as dichloromethane or chloroform.

The reaction may be carried out at a non-extreme temperature such as −60° C. to +60° C., preferably from −20° C. to 40° C., more preferably from 0° C. to +30° C. and conveniently at ambient temperature.

The azide ion may be introduced to the reaction as an inorganic azide for example sodium azide, or as an organic azide such as tetramethylguanidinium azide. Care must be exercised when selecting an appropriate azide as many azides, particularly heavy metal azides, are explosive.

This method is not preferred for compounds of the formula (I) wherein R is —CONR$^1$R$^2$.

The compound of the formula (IX) may be prepared by a process which comprises the reaction of a corresponding ester of a compound of the formula (X):

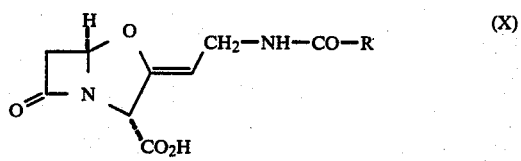

wherein R is as defined in relation to formula (II), with an imino-halogenating agent and a base.

The imino-halogenating agent used is one which will convert an amide group —NH—CO— to an imino-halide —N=CR$^{14}$— wherein $R^{14}$ is as hereinbefore defined, for example phosphorus pentachloride, phosphorus pentabromide, thionyl chloride, thionyl bromide, phosgene, phosphorus trichloride, phosphorus tribromide, phosphorus oxychloride or phosphorus oxybromide.

The solvent used is suitably an inert organic solvent such as dichloromethane, chloroform, carbon tetrachloride, dichloroethane, tetrahydrofuran or dioxan.

The reaction is performed in the presence of a base. Suitably the base is an organic base for example a tertiary amine such as triethylamine, trimethylamine or N-alkylmorpholine, and pyridine. Most suitably the organic base is N-methylmorpholine.

It is also possible to use triphenylphosphine or tri-p-methoxyphenylphosphine with carbon tetrahalide as an imino-halogenating agent, for example triphenylphosphine in carbon tetrachloride or triphenylphosphine and carbon tetrabromide in an organic solvent, for example dichloromethane, chloroform or benzene.

The compounds of the formula (X) may be prepared by the methods of Belgian Patent Nos. 860042 and 866496.

In a further aspect the present invention provides a process for the preparation of a compound of the formula (XI):

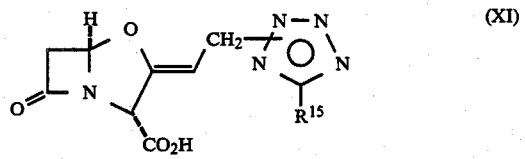

or salt or ester thereof wherein $R^{15}$ is an esterified or salified carboxy or a group CONR$^1$R$^2$ as hereinbefore defined, which process comprises the reaction of a compound of the formula (XII):

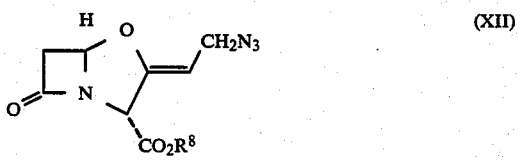

wherein $R^8$ is as hereinbefore defined, with a reactive nitrile of the formula (XIII):

$$R^{15}-C\equiv N \tag{XIII}$$

and thereafter if necessary:
(i) converting any ester group into a carboxylic acid or salt;
(ii) converting a carboxylic acid or salt into an in-vivo hydrolysable ester.
(iii) converting a compound of the formula (II) wherein $R^{15}$ is esterified or salified carboxy into a compound of the formula (II) wherein $R^{15}$ is hydrogen.

Suitably $R^{15}$ is a conjugating group, for example an esterified carboxy group of the sub-formula (ii):

$$R^{16}O_2C- \tag{ii}$$

wherein $R^{16}$ is an esterifying group. Suitably $R^{16}$ is an ester of the sub-formulae (b), (c), (d) or (e). Preferably $R^{16}$ is optionally substituted $C_{1-6}$alkyl or optionally substituted benzyl, for example methyl, ethyl or benzyl.

Suitably the reaction is performed at a temperature between 0° C. and 120° C., preferably between 50° C. and 100° C. The reaction may be performed in the absence of solvent (if the compound of the formula (XIII) is a liquid) or alternatively in the presence of solvent, suitably an organic solvent. Suitable solvents include inert organic solvents such as tetrahydrofuran and chloroform.

The compounds of the formula (XII) may be prepared by the methods of Belgian Pat. No. 855,375.

The following Examples illustrate the invention.

EXAMPLE 1

Benzyl 9-tetrazol-2-yldeoxyclavulanate

To a solution of benzyl clavulanate (2.89 g) in tetrahydrofuran (50 ml), triphenylphosphine (3.14 g) and tetrazole (1.4 g) were added. The mixture was stirred until all was in solution, cooled to 2°–5° C. in an ice-bath and diethyl azodicarboxylate (2.1 ml) added all at once. The reaction mixture was stirred for 30 mins at ambient temperature then evaporated to small volume. Ethyl acetate and cyclohexane (50 ml, about 1:1) were added and the colourless crystalline precipitate filtered off; the filtrate was re-evaporated and subjected to gradient elution chromatography on silica gel using ethyl acetate and cyclohexane graded from 3:1 to 1:1 ratio. The second major β-lactam-containing component was separated, and fractions containing it were combined and evaporated under reduced pressure on a rotary evaporator. The residue (which contained some diethyl hydrazodicarboxylate) was treated with $CCl_4$ (ca. 1 ml), filtered and the filtrate evaporated, to yield the title product as an oil, 0.24 g, still containing a little solvent.

Infra-red (film) 1805 (β-lactam C=O), 1755 (ester C=O) and 1705 cm$^{-1}$ (C=C)

EXAMPLES 1 (a)–(f)

(a) Diethylazodicarboxylate may be replaced by di-tert-butyl azodicarboxylate to yield the title compound (0.07 g).
(b) Diethylazodicarboxylate may be replaced by diisopropyl azodicarboxylate to yield the title compound (0.1 g).
(c) Diethylazodicarboxylate may be replaced by dimethyl azodicarboxylate (2 ml) to yield the title compound (0.19 g).
(d) Diethylazodicarboxylate may be replaced by ethyl diazoacetate (1.4 ml), the reaction being stirred at 2°–3° C. for 2 days to yield the title compound (0.05 g).
(e) Diethylazodicarboxylate may be replaced by diphenyl diazomethane, in excess, the reaction being warmed to 50° C. for one hour, the title compound being detected by t.l.c.
(f) Triphenyl phosphine may be replaced by tributylphosphine (~2 g) to yield the title compound (0.1 g).

EXAMPLE 2

Methoxymethyl 9-tetrazol-2-yldeoxyclavulanate

In a method analogous to that of Example 1, substituting methoxymethyl clavulanate (5.1 g) for benzyl clavulanate, with the same ratios of reagents the title compound was obtained as a pale yellow oil (0.11 g), i.r. (liq film) 1795 (β-lactam), 1745 (ester), 1700 (C=C) cm$^{-1}$.

EXAMPLE 3

Methyl 9-tetrazol-2-yldeoxyclavulanate

In a method analogous to that of Example 1, substituting methyl clavulanate (2.12 g) for benzyl clavulanate with the same ratios of reagents, the title compound was obtained (0.25 g), i.r. (liq film) 1795 (β-lactam), 1740 (ester), 1695 (C=C) cm$^{-1}$.

EXAMPLE 4

4-Bromobenzyl 9-tetrazol-2yldeoxyclavulanate

In a method analogous to that of Example 1 substituting 4-bromobenzyl clavulanate (3.7 g) for benzyl clavulanate, with the same ratios of reagents the title compound was obtained (0.24 g). i.r. (liq. film) 1807 (β-lactam), 1755 (ester), 1707 (C=C) cm$^{-1}$.

EXAMPLE 5

4-Nitrobenzyl 9-tetrazol-2-yldeoxyclavulanate

In a method analogous to that of Example 1 substituting 4-nitrobenzyl clavulanate (8.4 g) for benzyl clavulanate, with the same ratios of reagents the title compound was obtained (1.0 g), i.r. (liq. film) 1800 (β-lactam), 1750 (ester), 1695 (C=C) cm$^{-1}$.

EXAMPLE 6

Benzyl 9-(tetrazol-2-yl)deoxyclavulanate and Benzyl 9-(tetrazol-1-yl)deoxyclavulanate To a stirred solution of benzyl clavulanate (11.8 g) in dry redistilled tetrahydrofuran (175 ml) was added tetrazole (5.0 g) and triphenylphosphine (12.3 g). When the reactants had dissolved, the mixture was cooled to 2°–3° C. in an ice-bath, then diethyl azodicarboxylate (9 ml) was added rapidly from a pipette. The mixture was stirred at ambient temperature for 30 mins, at which time tlc showed a number of $KMnO_4$—positive zones. The reaction mixture was evaporated under reduced pressure to about 70 ml, then re-evaporated with two successive portions of 50 ml of toluene until reduced to a syrup containing crystalline material. 100 ml of toluene was added, cooled to 2°–3° C., filtered off insolubles and the filtrate re-evaporated. The mixture was subjected to gradient elution chromatography on silica gel, using a short wide column, eluted with ethyl acetate and n-hexane graded from 1:2 to 2:1 ratio. After an initial fractionation into more polar and less polar products, the latter were combined and rechromatographed on a similar column. Fractions containing benzyl 9-(tetrazol-2-yl)deoxyclavulanate were collected and combined to yield 0.9 g of an oil; I.r. (film) 1805 (β-lactam C=O) 1755 (ester C=O) and 1705 cm$^{-1}$ (C=C); nmr; δ (CDCl$_3$) 3.09 (1H,d, J 17 Hz, 6-β-CH) 3.52 (1H, dd, J 17 and 3 Hz, 6-α-CH), 4.9–5.4 (6H, m, including s. for PhCH$_2$ at 5.16, PhCH$_2$, 3-CH, 8-CH, 9-CH$_2$), 5.77 (1H,d, J 3 Hz, 5-CH), 7.30(5H, Ph), 8.47 (1H, s, tetrazole CH). The more polar products were rechromatographed using a reverse gradient on silica gel, the solvent being graded from ethyl acetate to 4:1 ethyl acetate:cyclohexane. The fractions containing benzyl 9-(tetrazol-1-yl)deoxyclavulanate were collected and combined to yield 0.15 g of a slightly impure oil; i.r. (film) 3140 (tetrazole CH), 1802(β-lactam C=O), 1748 (ester C=O) and 1700 cm$^{-1}$ (C=C).

EXAMPLE 7

Lithium 9-tetrazol-2-yldoexyclavulanate

A solution containing benzyl 9-tetrazol-2-yldeoxyclavulanate (0.48 g, containing a little inert solvent) in redistilled tetrahydrofuran (30 ml) and water (1 drop) was hydrogenated at ambient temperature and pressure over 10% palladised charcoal for 2 hours, when the uptake of hydrogen had ceased. The catalyst was removed by filtration, washed with a little tetrahydrofuran, the filtrate diluted with water (100 ml) and titrated with 1.0M aqueous lithium hydroxide to pH 7.5. The mixture was evaporated under reduced pressure to small volume (>1 ml) diluted with 1-propanol (10 ml) and re-evaporated to dryness to leave a pale buff crystalline solid. This was triturated with acetone and collected by filtration, washed with ether and dried in vacuo, to yield 0.19 g of the title compound.

I.R. spectrum (nujol) 1785(β-lactam C=O), 1700(C=C) and 1620 cm$^{-1}$(CO$_2^-$).

This compound may be hydrated.

EXAMPLE 8

Lithium 9-(tetrazol-2-yl)deoxyclavulanate

Methyl 9-tetrazol-2-yldeoxyclavulanate (250 mg) in THF—water was maintained at pH 9.5 at the pH-Stat by the addition of 1M lithium hydroxide. When uptake became slow the reaction was stopped, and the mixture evaporated to a small volume under reduced pressure. The residue was triturated under acetone and the lithium salt filtered off, washed with acetone and dried to afford the title compound. Ir (film of DMSO solution) 1778 cm$^{-1}$(β-lactam C=O).

EXAMPLE 9

Benzyl 9-(5-aminotetrazolyl)deoxyclavulanate 5-aminotetrazole monohydrate was dehydrated by heating in a Dean and Starke apparatus using toluene to co-distil the water. When no further water distilled, the suspension was cooled to room temperature, decanted off the toluene, added dry ether and decanted again, finally dried in vacuo over P$_2$O$_5$; 2.3 g of this material was dissolved in about 8 ml of warm dry N,N-dimethylformamide.

A solution of benzyl clavulanate (2.89 g) in dry tetrahydrofuran (70 ml) containing triphenylphosphine (3.14 g) was cooled in ice-water and stirred. To this solution were added successively the 5-aminotetrazole solution and then diethyl azodicarboxylate (2.1 ml). The mixture was stirred for 30 mins, then evaporated under reduced pressure. Most of the dimethylformamide was then removed by evaporation at 0.2 mm pressure. The residue was diluted with ethyl acetate—cyclohexane (1:1, about 50 ml), and the precipitated solids removed by filtration. The filtrate was re-evaporated, and subjected to gradient elution chromatography on silica gel using ethyl acetate and cyclohexane mixtures, graded from 1:2 ratio through 2:1 ratio to pure ethyl acetate, as elution solvent. The most polar β-lactam-containing product (as determined by tlc (SiO$_2$) in 2:1 ethyl acetate—cyclohexane) was collected, and fractions containing it were combined and evaporated, to yield 140 mg of an oil containing some N,N-dimethylformamide. This was not further purified.

Infra-red spectrum (film) 3600–2800 (broad, with fine structure, NH$_2$), 1805 (β-lactam C=O), 1760 (ester C=O), 1705 cm$^{-1}$ (C=C).

The above reaction was repeated on a larger scale, using benzyl clavulanate (11.56 g) and the same ratio of reactants, to afford the title compound as a crude product (0.7 g). This crystallised on standing, and after trituration with carbon tetrachloride, the product was collected by filtration, washed with a little further carbon tetrachloride and dried in vacuo to yield the title product (0.49 g); i.r. (Nujol mull) 3335, 3260(NH$_2$), 1800(β-lactam C=O), 1753 (ester C=O), 1712 cm$^{-1}$(C=C). This compound is believed to be the 1-tetrazole isomer.

EXAMPLE 10

Lithium 9-(5-aminotetrazolyl)deoxyclavulanate

The partially purified benzyl ester of example 9 (140 mg) was dissolved in redistilled tetrahydrofuran (10 ml) containing water (1 drop) and 10% palladised charcoal (70 mg). It was hydrogenated at ambient temperature and pressure for about 1 hour. The catalyst was removed by filtration, washed with water and the filtrate and washings diluted with water and titrated to pH 7.3 with lithium hydroxide solution. The solution was evaporated to near dryness, 1-propanol added and re-evaporated to dryness. The colourless crystalline solid was triturated with acetone filtered off, washed with acetone and dried in vacuo, to yield the title compound (30 mg).

Infra-red spectrum (mull) 1790(β-lactam C=O), 1705 (C=C) and 1640 (broad, CO$_2^-$).

EXAMPLE 11

Benzyl 9-(5-acetamidotetrazolyl)deoxyclavulanate

To a solution of benzyl clavulanate (2.89 g) and triphenylphosphine (3.14 g) in dry redistilled tetrahydrofuran (50 ml), stirred and cooled in ice+water, were added a solution of 5-acetamidotetrazole (2.5 g) in N,N-dimethylformamide (20 ml) and immediately diethyl azodicarboxylate (2.2 ml). Allowed to stir for 30 mins, evaporated to low volume. Ethyl acetate and cyclohexane (60 ml, 1:1) were added, then washed with water (2×60 ml portions), to remove DMF and other water-soluble materials. The solvent layer was dried over sodium sulphate, filtered, evaporated to a syrup and subjected to gradient elution chromatography on silica gel using ethyl acetate and cyclohexane, graded from 2:1 to neat ethyl acetate, as eluents. Fractions containing the most polar β-lactam-containing component were collected and combined, to yield the title compound as an oil (100 mg).

Infra-red spectrum (film) 1800 (β-lactam C=O), 1745 (ester C=O), 1700 (C=C).

EXAMPLE 12

Sodium 9-(5-acetamidotetrazolyl)deoxyclavulanate

A solution of the benzyl ester of example 11 (0.1 g) in redistilled tetrahydrofuran (15 ml) was hydrogenated at ambient temperature and pressure over 10% palladised charcoal (50 mg) for about 1 hour (tlc at this time showed that some ester remained, but the reaction was worked up notwithstanding). The catalyst was removed by filtration, the filtrate diluted with water (50 ml) and titrated to pH 7.3 with 0.5M NaOH solution. The solution was evaporated to dryness, and triturated with acetone. The colourless crystalline product was filtered off, crushed quickly with acetone and dried in vacuo. It was somewhat hygroscopic. Yield 25 mg.

Infra-red spectrum (mull) 1780 ($\beta$-lactam C=O), 1700 (shoulder, C=C), 1690 (NHCO), and 1620 cm$^{-1}$ ($CO_2^-$).

EXAMPLE 13

Benzyl 9-(5-ethoxycarbonyltetrazol-1-yl)-deoxyclavulanate

To benzyl 9-azidodeoxyclavulanate (4 g) was added ethyl cyanoformate (10 ml). The mixture was heated under reflux in an oil-bath at 80°–100° for 1½ days. The tlc ($SiO_2$, 1:1 hexane-ethyl acetate) of the mixture at this stage showed some unreacted 9-azido compound. The excess ethyl cyanoformate was evaporated in vacuo, and the residue subjected to gradient elution chromatography on silica gel, using ethyl acetate and hexane (or cyclohexane) graded from 1:2 to 2:1 ratio. The unreacted azide eluted first. Those fractions which contained mainly the 1-tetrazole were combined, diluted with approximately an equal volume of cyclohexane and cooled to 2°–3° C. The compound crystallised and it was collected by filtration, washed with ether and dried in vacuo. The yield of benzyl 9-(5-ethoxycarbonyltetrazole-1-yl)deoxyclavulanate was 1.3 g; mp 100° C.; Ir (mull) 1798, ($\beta$-lactam C=O) 1740 (esters) 1688 cm$^{-1}$ (C=C). Nmr ($CD_3COCD_3;CDCl_3$ was unsuitable) $\delta$ 1.39 (3H, t, J 7 Hz, $CH_3CH_2$), 3.10 (1H, d, J 17 Hz, 6-$\beta$-CH), 3.64 (1H, dd, J 17 and 3 Hz, 6-$\alpha$ CH), 4.47 (2H, q, J 7 Hz, $CH_3CH_2$), 5.05 (1H, t, J 8 Hz, 8-CH=), 5.18 (2H, s, $PhCH_2$), 5.23 (1H, s, 3-CH), 5.44 (2H, d, J 8 Hz, 9-$CH_2$) 5.81 (1H, d, J 3 Hz, 5-CH) and 7.33 (5H, s, Ph).

EXAMPLE 14

Lithium 9-(5-ethoxycarbonyltetrazol-1-yl)deoxyclavulanate and sodium 9-(5-ethoxycarbonyltetrazol-1-yl)deoxyclavulanate A solution of benzyl 9-(5-ethoxycarbonyltetrazol-1-yldeoxyclavulanate (1 g) in redistilled tetrahydrofuran (25 ml) containing water (~0.1 ml) and 10% palladised charcoal (0.5 g) was hydrogenated at ambient temperature and pressure. Uptake of hydrogen was very rapid (about 1 minute). The catalyst was removed by filtration, then the filtrate was diluted with water and titrated to pH 7.3 with IM lithium hydroxide solution. The solvents and water were removed under reduced pressure until a syrup remained; this began to crystallise. It was diluted slowly with acetone, filtered off, washed with acetone and dried in vacuo. (A small sample was air-dried for Karl Fischer water determination; it contained 10%, equivalent to a dihydrate). Yield 0.76 g.

Nmr ($D_2O$) $\delta$: 1.33 (3H, t, J 7 Hz, $CH_3CH_2$) 2.12 (acetone) 2.98 (1H, d, J 17 Hz, 6-$\beta$-CH) 3.47 (1H, dd, J 17 and 3 Hz, 6-$\alpha$-CH) 4.47 (partially obscured by HOD, q, J 7 Hz, $CH_3CH_2$), 4.90 (1H, s, 3-CH) 8-CH probably about 5.18, 5.4 (2H, d, J 8 Hz, 9-$CH_2$) and 5.66 (1H, d, J 3 Hz, 5-CH). Ir. (mull): 1782 ($\beta$-lactam C=O) 1735 (ester C=O) 1690 (C=C) and 1625 cm$^{-1}$ ($CO_2^-$).

The sodium salt was obtained analogously by neutralisation of the filtered hydrogenation solution using aqueous sodium hydroxide solution. It was also a crystalline solid, and hydrated. I.r. (mull) 1785 ($\beta$-lactam C=O) 1735 (ester C=O) 1690 (C=C) 1620 cm$^{-1}$ ($CO_2^{31}$).

EXAMPLE 15

Disodium 9-(5-carboxylatotetrazol-1-yl)deoxyclavulanate

A solution of 0.1 g of sodium 5-ethoxycarbonyltetrazol-1-yldeoxyclavulanate in 10 ml of water was maintained at pH 9.5 on a pH—stat by the addition of 0.05M aqueous sodium hydroxide solution, until the uptake of alkali became very slow. The solution was evaporated under reduced pressure, the residue triturated with acetone and then filtered off, washed with ether and dried. I.r. spectrum (mull) 1775 ($\beta$-lactam C=O) 1690 (sh) (C=C) 1655 and 1605 cm$^{-1}$ ($CO_2^-$). Nmr ($D_2O$) $\delta$ 2.98 (1H, d, J 17 Hz, 6-$\beta$-CH), 3.45 (1H, dd, J 17 and 3 Hz, 6-$\alpha$-CH), 4.75–5.4 (5H, m, 3-CH, 9-$CH_2$, 8-CH), and 5.63 (1H, d, J 3 Hz, 5-CH).

EXAMPLE 16

Benzyl 9-(tetrazol-1-yl)deoxyclavulanate

A solution of benzyl 9-(5-ethoxycarbonyltetrazol-1-yl)deoxyclavulanate (1 g) in redistilled tetrahydrofuran (20 ml) was diluted with water until the first permanent turbidity appeared. The solution was then stirred and maintained at pH 9–9.5 at a pH—Stat by the addition of IM lithium hydroxide (about 2 ml). The mixture was diluted with water (100 ml) extracted with several portions of ethyl acetate (each 50 ml), then dichloromethane (100 ml) was added and the mixture acidified to pH 1 by the addition of 2.5M $H_2SO_4$. The aqueous layer was re-extracted with ethyl acetate, then the solvent layers combined, dried ($Na_2SO_4$) and evaporated. The residue was subjected to gradient elution chromatography on silica gel, using ethyl acetate and cyclohexane graded from 1:1 ratio to neat ethyl acetate as eluents. The product was the most polar $\beta$-lactam-containing component, having an $R_f$ (1:1 ethyl acetate-hexane)>0.1. About 50 mg of the pure ester was obtained after evaporation of solvent, though some further fractions contained the compound in a less pure state. It was an oil, Ir (film): 3140 (tetrazole C-H stretch), 1807 ($\beta$-lactam C=O), 1755 (ester C=O) and 1705 cm$^{-1}$ (C=C). Nmr ($CDCl_3$) $\delta$: 3.07 (1H, d, J 17 Hz, 6-$\beta$-CH), 3.53 (1H, dd, J 17 and 3 Hz, 6-$\alpha$-CH), 4.8–5.4 (6H, m, 9-$CH_2$, 3-CH, 8-CH, $PhCH_2$) 5.76 (1H, d, J 3 Hz, 5-CH), 7.33 (5H, s, $C_6H_5$) and 8.38 (1H, d, tetrazole CH); the tetrazole 5-H signal shifts to about $\delta$ 9.2 in $D_6$-acetone.

EXAMPLE 17

Dipotassium 9-(5-carboxytetrazol-1-yl)deoxyclavulanate

A solution of benzyl 9-(5-ethoxycarbonyltetrazol-1-yl)deoxyclavulanate (6.2 g) in redistilled tetrahydrofuran (30 ml) containing water (0.1 ml) was hydrogenated at ambient temperature and pressure over 10% palladium on charcoal (1.6 g) until uptake of hydrogen became very slow. The catalyst was removed by filtration through silica, the filtrate diluted with water (100 ml) and titrated to pH 7 with 1M sodium hydroxide. Most of the tetrahydrofuran was evaporated under reduced pressure, and the aqueous solution then maintained at pH 9–9.5 by the automatic addition of 1M NaOH solution until the uptake of alkali became slow. The solution was acidified by the addition of pre-washed IR120 (H+) resin in two portions, decanting each time, to give a pH of 1.5–1.7, then neutralised to pH 7.2 by the addition of 1M KOH. The solution was evaporated to crystallisation, isopropanol and acetone added (about 1 Lit. total), the solid was filtered off, washed with acetone and dried in vacuo, to yield 3.6 g of the title compound as a colourless crystalline solid; Ir (Nujol mull) 3500, 3400 (broad, $H_2O$ of crystallisation) 1775 ($\beta$-lactam C=O) 1698 (C=C) 1665 and 1615 $cm^{-1}$ ($CO_2^-$).

EXAMPLE 18

Lithium 9-(tetrazol-1-yl)deoxyclavulanate

A solution of disodium 9-(5-carboxytetrazol-1-yl)deoxyclavulanate (1.0 g) in water (50 ml) was layered with ethyl acetate (100 ml) and saturated with sodium chloride. The mixture was vigorously stirred and acidified to pH 1.0 by the addition of 1M hydrochloric acid. The layers were separated and the aqueous layer extracted with further 2×75 ml portions. The ethyl acetate extracts were combined, dried over a little anhydrous sodium sulphate, filtered and added to water (50 ml). The mixture was stirred vigorously and titrated to pH 7.3 with 1M lithium hydroxide solution. The layers were separated, the solvent layer washed with a little water and the aqueous extracts combined, diluted with an equal volume of 1-propanol and evaporated to dryness under reduced pressure. The crystalline pale orange residue was triturated with acetone, filtered off, washed and dried in vacuo, to yield 0.65 g of the title product as a pale apricot coloured crystalline solid; I.R. (Nujol mull) 3400 (very broad, $H_2O$), 3120 (tetrazole CH stretch), 1785 ($\beta$-lactam C=O), 1702 (C=C) and 1610 $cm^{-1}$ (broad, $CO_2^-$): NMR $\delta$ ($D_2O$, $CH_3CN=2.0$) 3.04 (1H, d, J 3 Hz, 6-$\beta$-CH), 3.52 (1H, dd, J 3.0 and 17 Hz, 6-$\alpha$-CH), 4.97 (1H, s, 3-CH), 5.0–5.25 (3H, m, 8-CH and 9-$CH_2$), 5.73 (1H, d, J 3.0 Hz, 5-CH) and 9.09 (1H, s, tetrazole CH).

EXAMPLE 19

Sodium 9-(tetrazol-1-yl)deoxyclavulanate

The procedure of Example 18 was repeated using sodium hydroxide solution in place of lithium hydroxide solution. The product was a hygroscopic solid; Ir (Nujol mull) 3400 (broad, $H_2O$), 3140 (weak, tetrazole CH stretch) 1785 ($\beta$-lactam C=O) 1698 (C=C), 1620 and 1580 $cm^{-1}$ ($CO_2^-$).

EXAMPLE 20

Potassium 9-(tetrazol-1-yl)deoxyclavulanate

The procedure of Example 18 was repeated using potassium hydroxide solution in place of lithium hydroxide solution. The product was obtained from slightly aqueous acetone or isopropanol. It was very slightly hygroscopic.

EXAMPLE 21

Potassium 9-(tetrazol-1-yl)deoxyclavulanate

A solution of dipotassium 9-(5-carboxytetrazol-1-yl)deoxyclavulanate (3.3 g) in water (100 ml) was layered with 300 ml of ethyl acetate. To it was added sufficient 'Amberlite' IR 120 (H+) resin (prewashed with dilute $H_2SO_4$ and then washed with water until almost neutral) to give pH 1.5–1.8. The mixture was allowed to stir for 1 hour at ambient temperature (about 20° C.), then decanted from the resin. The resin was washed with a little water, which was added to the solution. The mixture was titrated to pH 7.2 with 1M KOH solution, the layers separated and the aqueous layer evaporated to near dryness, diluted slowly with isopropanol-acetone and cooled to 2°–3° C. when crystallisation occurred. The compound was filtered off, washed with acetone and dried in vacuo, to yield 1.7 g of the potassium salt.

The compound was further purified by solution in a small volume of water and treatment with activated charcoal. After filtration to remove charcoal the filtrate was diluted with acetone or isopropanol; after seeding, scratching and cooling the pure colourless potassium salt crystallised and was collected, washed with acetone and dried, to yield 1.1 g. A further 0.3 g was obtained from the mother liquor by evaporation and trituration with acetone: Infrared spectrum of potassium salt (Nujol mull) 3400 (weak, br, $H_2O$) 3120 (weak, tetrazole C-H stretch) 1785 ($\beta$-lactam C=O) 1695 (C=C, sharp and rather strong), 1627 and 1605 $cm^{-1}$, ($CO_2^-$, strong). Other strong unassigned peaks in the spectrum were at 1294, 1172, 1034, 788, 756 and 676 $cm^{-1}$; numerous other sharp peaks.

EXAMPLE 22

Sodium 9-(tetrazol-1-yl)deoxyclavulanate

A solution of mixed lithium and potassium salts (1.2 g, about 2:3) in water (10 ml) was passed down a column of IR120 (Na+ form) that had been thoroughly washed with water. The eluate was collected and evaporated to near dryness; 1-propanol was added and re-evaporated. The solid residue was triturated with acetone-ether, filtered off quickly, washed with dry ether and dried in vacuo, to yield 1.0 g of sodium salt.

EXAMPLE 23

Benzyl 9-(5'-methyltetrazol-1'-yl)deoxyclavulanate (i) Benzyl 9-acetamido-9-deoxyclavulanate Benzyl-9-azido-9-deoxyclavulanate (2 g) was dissolved in tetrahydrofuran (40 ml)/water (20 ml) and the solution ice cooled and stirred vigorously. Zinc powder (5 g) was added in small quantities over 1½ hours, while maintaining the pH of the solution between 3 and 4 by dropwise addition of 2N HCl. When benzyl 9-azido-9-deoxyclavulanate could no longer be detected in the solution (silica tlc, eluent ethyl acetate/petroleum ether 1:2), the pH was adjusted to 6 with 1N aqueous sodium bicarbonate and the solution filtered. The filtrate was saturated with NaCl and extracted with ethyl acetate (3×30 ml). The combined ethyl acetate extracts were dried over $MgSO_4$ and evaporated under reduced pressure to ca. 50 ml to provide a solution containing benzyl 9-amino-9-deoxyclavulanate. This solution was treated with acetic anhydride (1.0 ml) and pyridine (0.52 ml), stirred 1 hour at room temperature, washed with 0.1N HCl (50 ml), 1N aqueous sodium bicarbonate solution (50 ml) and water (50 ml), dried over MgSO$_4$ and evaporated under reduced pressure. The residue was chromatographed on silica, eluting with ethyl acetate, to provide benzyl 9-acetamido-9-deoxyclavulanate as a white solid (1.47 g). This was crystallised from ethyl acetate. Found C 61.8, H 5.5, N 8.5%. C$_{17}$H$_{18}$N$_2$O$_5$ requires C 61.8, H 5.5, N 8.5%; $\nu_{max}$(CHCl$_3$) 3440, 1800, 1750, 1690, 1660, 1505 cm$^{-1}$.

(ii) Benzyl 9-(5'-methyltetrazol-1'-yl)-9-deoxyclavulanate

Benzyl 9-acetamido-9-deoxyclavulanate (0.40 g, 1.21 mmole) was dissolved in dry dichloromethane (7 ml) and ice cooled. This solution was treated with pyridine (0.195 ml, 2.42 mmole) and then with a 12.5% solution of phosgene in toluene (1.48 ml). After stirring at room temperature for 80 minutes, the solution was evaporated under reduced pressure and the residue quickly dissolved in dry dichloromethane (10 ml). This solution was ice cooled, treated with tetramethylguanidinium azide (0.47 g, 3.02 mmole) and then stirred at room temperature for 30 minutes. The resulting solution was washed with 0.5N HCl (10 ml) and brine (10 ml), dried over MgSO$_4$ and evaporated under reduced pressure. The residue was chromatographed on silica, eluting with ethyl acetate/petroleum ether 3:1, and appropriate fractions were combined and evaporated to provide benzyl 9-(5'-methyltetrazol-1'-yl)-9-deoxyclavulanate as a colourless gum (0.286 g). [α]$_D^{20}$+29.8° (c.1.0; CHCl$_3$); $\nu_{max}$ (CHCl$_3$) 1805, 1750, 1695 cm$^{-1}$; δ (CDCl$_3$) 2.39 (3H, s, —CH$_3$), 3.06 (1H, d, J 17 Hz, 6β-CH), 3.54 (1H, dd, J 17 and 2.5 Hz, 6α-CH), 4.7–5.0 (3H, m, 8-CH and 9-CH$_2$), 5.0–5.3 (3H, m, 3-CH and —OCH$_2$Ph), 5.73 (1H, d, J 2.5 Hz, 5-CH), 7.29 (5H, s, Ph-H); Found 355.1272: C$_{17}$H$_{17}$N$_5$O$_4$ requires 355.1280.

EXAMPLE 24

Benzyl 9-(5'-methyltetrazol-1'-yl)-9-deoxyclavulanate

Benzyl 9-acetmido-9-deoxyclavulanate (0.10 g, 0.303 mmole) was dissolved in dry dichloromethane (5 ml) and ice cooled. The solution was treated with pyridine (0.081 ml) and phorphorus pentachloride (0.066 g, 0.318 mmole) and stirred 30 minutes at 0°–5° C. Tetramethylguanidinium azide (0.156 g, 1 mmole) was then added and the solution stirred a further 30 minutes at 0°–5° C., washed with 0.5 NHCl (10 ml), dried over MgSO$_4$ and evaporated under reduced pressure. The residue was chromatographed as in example 23 to provide benzyl 9-(5'-methyltetrazol-1'-yl)-9-deoxyclavulanate (0.08 g), identical to the product of example 23.

EXAMPLE 25

Potassium 9-(5'-methyltetrazol-1'-yl)-9-deoxyclavulanate

Benzyl 9-(5-methyltetrazol-1-yl)-9-deoxyclavulanate (0.28 g, 0.79 mmole) was dissolved in distilled tetrahydrofuran (15 ml), treated with 10% palladium/charcoal (90 mg) and hydrogenolysed for 30 minutes at atmospheric pressure. The suspension was filtered through celite and the filtrate evaporated under reduced pressure to 2 ml. Water (15 ml) was added and this solution was brought to pH 7 by dropwise addition of 0.5N aqueous KOH, washed with ethyl acetate (2×10 ml), concentrated to ca. 5 ml under reduced pressure and freeze dried. Potassium 9-(5'-methyltetrazol-1'-yl)-9-deoxyclavulanate was obtained as a yellow solid (0.234 g). $\nu_{max}$ (KBr) 1780, 1690, 1610 cm$^{-1}$; δ (D$_2$O): HO-D=4.60δ) 2.48 (3H, s, —CH$_3$), 3.02 (1H, d, J 17 Hz, 6β-CH), 3.52 (1H, dd, J 17 and 2.5 Hz, 6α-CH), 4.6–5.1 (4H, m, 3-CH), 8-CH and 9-CH$_2$), 5.70 (1H, d, J 2.5 Hz, 5-CH).

EXAMPLE 26

Benzyl 9-(5'-phenyltetrazol-1'-yl)-9-deoxyclavulanate

Benzyl 9-benzamido-9-deoxyclavulanate (0.25 g, 0.64 mmole) was dissolved in dry dichloromethane (15 ml) and ice cooled. The solution was treated with pyridine (0.52 ml) and then with a 12.5% solution of phosgene in toluene (5.6 ml). This mixture was stirred at room temperature for 18 hours, evaporated under reduced pressure and the residue quickly redissolved in dry dichloromethane (15 ml). This solution was ice cooled, stirred and treated with tetramethylguanidinium azide (0.203 g, 1.3 mmole). Stirring was continued for 1¼ hours at room temperature and the resulting solution was washed with 0.5N hydrochloric acid (20 ml) and brine (20 ml), dried over MgSO$_4$ and evaporated under reduced pressure. The residue was chromatographed on silica, eluting with ethyl acetate/petroleum ether 1:2, and appropriate fractions were combined and evaporated to provide benzyl 9-(5'-phenyltetrazol-1'-yl)-9-deoxyclavulanate (0.182 g) as a colourless gum. [α]$_D^{20}$+21.2° (c.1.3; CHCl$_3$); $\nu_{max}$ (CHCl$_3$) 1805, 1750, 1695 cm$^{-1}$; δ (CDCl$_3$) 2.95 (1H, d, J 17 Hz, 6β-CH), 3.47 (1H, dd, J 17 and 2.5 Hz, 6α-CH) 4.7–4.95 (1H, m, 8-CH), 4.95–5.3 (5H, m, -OCH$_2$Ph, 9-CH$_2$, 3-CH), 5.63 (1H, d, J 2.5 Hz, 5-CH), 7.25 (5H, s, Ph-H), 7.3–7.7 (5H, m, Ph-H); Found 417.1456: C$_{22}$H$_{19}$N$_5$O$_4$ requires 417.1438.

EXAMPLE 27

Potassium 9-(5'-phenyltetrazol-1'-yl)-9-deoxyclavulanate

Benzyl 9-(5'-phenyltetrazol-1'-yl)-9-deoxyclavulanate (0.18 g, 0.433 mole) was dissolved in distilled tetrahydrofuran (10 ml), treated with 10% palladium/charcoal (50 mg) and hydrogenolysed for 30 minutes at atmospheric pressure.

The suspension was filtered through celite and the filtrate evaporated under reduced pressure to 2 ml. Water (5 ml) was added and this solution was brought to pH 7 by dropwise addition of 0.5N aqueous KOH, washed with ethyl acetate (2×10 ml), concentrated to ca. 5 ml under reduced pressure and freeze dried. Potassium 9-(5'-phenyltetrazol-1'-yl)-9-deoxyclavulanate was obtained as a yellow solid (0.11 g). $\nu_{max}$ (KBr) 1775, 1695, 1610 cm$^{-1}$; δ (D$_2$O:HOD=4.60δ) 2.80 (1H, d, J 17 Hz, 6β-CH), 3.44 (1H, dd, J 17 and 2.5 Hz, 6α-CH), 4.6–4.9 (2H, m, 3-CH and 8-CH), 5.0–5.2 (2H, m, 9-CH$_2$), 5.51 (1H, d, J 2.5 Hz, 5-CH), 7.54 (5H, s, Ph-H).

EXAMPLE 28 tert-Butyldiphenylsilyl 9-(tetrazol-2-yl)deoxyclavulanate (i) tert-Butyldiphenylsilyl clavulanate A solution of clavulanic acid (1.25 mmole) in distilled tetrahydrofuran (4 ml) was treated with triethylamine (0.173 ml, 1.25 mmole) and then with tert-butyldiphenylsilyl chloride (0.325 ml, 1.25 mmole). After stirring at room temperature for 15 minutes, the suspension was filtered and the filtrate evaporated under reduced pressure. The residue was chromatographed on silica, eluting with ethyl acetate/petroleum ether 1:2, and appropriate fractions were combined and evaporated under reduced pressure to provide tert-butyldiphenylsilylclavulanate (0.36 g) as a colourless gum. $v_{max}$ (CHCl$_3$) 1800, 1735, 1690 cm$^{-1}$; δ (CDCl$_3$) 1.13 (9H, s, tBu), 1.65 (1H, br.s, OH), 3.14 (1H, d, J 17 Hz, 6β-CH), 3.53 (1H, dd, J17 and 2.5 Hz, 6α-CH), 4.24 (2H, d, J 7.5 Hz, 9-CH$_2$), 4.8-5.3 (2H, m, 3-CH and 8-CH), 5.70 )1H, d, J 2.5 Hz, 5-CH), 7.3-7.9 (10H, m, Ph-H).

(ii) tert-Butyldiphenylsilyl 9-(tetrazol-2-yl)deoxyclavulanate

A mixture of tert-butyldiphenylsilylclavulanate (0.437 g, 1 mmole), tetrazole (0.14 g, 2 mmole) and triphenylphosphine (0.314 g, 1.2 mmole) were dissolved in distilled tetrahydrofuran (5 ml) and the solution cooled to −20° C. under nitrogen. Diethylazodicarboxylate (0.197 ml, 1.2 mmole) was then added all at once and the mixture stirred while gradually warming to room temperature over 30 minutes. The solution was evaporated under reduced pressure and the residue chromatographed on silica, eluting with ethyl acetate/petroleum ether 1:2. Fractions containing the second major β-lactam containing component to be eluted were combined and evaporated under reduced pressure to provide tert-butyldiphenylsilyl 9-(tetrazol-2-yl)-9-deoxyclavulanate (0.06 g) as a colourless gum. $v_{max}$ (CHCl$_3$) 1800, 1735, 1695 cm$^{-1}$; δ (CDCl$_3$) 1.10 (9H, s, tBu), 3.10 (1H, d, J 17 Hz, 6β-CH), 3.57 (1H, dd, J 17 and 2.5 Hz, 6α-CH), 4.9-5.6 (4H, m, 3-CH, 8-CH and 9-CH$_2$), 5.80 (1H, d, J 2.5 Hz, 5-CH), 7.0-7.9 (10H, m, Ph-H), 8.50 (1H, s, tetrazol-H).

EXAMPLE 29

Lithium 9-(tetrazol-2-yl)-9-deoxyclavulanate tert-Butyldiphenylsilyl 9-(tetrazol-2-yl)-9-deoxyclavulanate (30 mg) was dissolved in distilled tetrahydrofuran (2.7 ml), ice cooled and treated with 1N aqueous hydrochloric acid (0.3 ml). The solution was stirred at room temperature for 45 minutes and saturated brine (10 ml) was added. The resulting mixture was extracted with ethyl acetate (2×10 ml) and the ethyl acetate dried over MgSO$_4$ and evaporated under reduced pressure. The residue was taken up in distilled tetrahydrofuran (2 ml)/water (2 ml) and the solution brought to pH 7 by dropwise addition of 0.2N LiOH solution. A further 5 ml water was added and the mixture washed with ethyl acetate (3×10 ml) and freeze dried to provide lithium 9-(tetrazol-2-yl)-9-deoxyclavulanate (16 mg) as a pale yellow solid identical with the product of example 7.

EXAMPLE 30

Triisopropylsilyl 9-(tetrazol-2-yl)-9-deoxyclavulanate (i) Triisopropylsilyl clavulanate A solution of clavulanic acid (9 mmol) in distilled tetrahydrofuran (40 ml) was stirred at room temperature and treated with triethylamine (1.25 ml) and then with triisopropylsilyl chloride (1.74 g). After stirring at room temperature for 15 minutes the suspension was filtered and the filtrate evaporated under reduced pressure. The residue was chromatographed on silica, eluting with ethyl acetate/hexane 2:3, and appropriate fractions were combined and evaporated under reduced pressure to provide triisopropylsilyl clavulanate (2.47 g) as a colourless oil. $v_{max}$ (CHCl$_3$) 1800, 1730, 1690 cm$^{-1}$; δ (CDCl$_3$), 0.8-2.0 (21H, m, (Pr$^i$)$_3$), 2.18 (1H, broad, s, -OH), 3.03 (1H, d, J 17 Hz, 6β-CH), 3.47 (1H, dd, J 17 and 2.5 Hz, 6α-CH), 4.23 (2H, broad d, J 7 Hz, 9-CH$_2$), 4.8-5.1 (2H, m, 3-CH and 8-CH), 5.67 (1H, d, J 2.5 Hz, 5-CH).

(ii) Triisopropylsilyl 9-(tetrazol-2-yl)-9-deoxyclavulanate

Triisopropylsilylclavulanate (1.20 g, 3.38 mmole), tetrazole (0.5 g, 7.15 mmole) and triphenylphosphine (1.06 g, 4.05 mmole) were dissolved in distilled tetrahydrofuran (20 ml), cooled to −10° C. and treated with diethylazodicarboxylate (0.665 ml, 4.05 mmole). The mixture was stirred for 15 minutes while warming to about 10° C. and evaporated under reduced pressure. The residue was chromatographed on silica, eluting with ethyl acetate/hexane 1:2. Fractions containing the second major β-lactam containing component to be eluted were combined and evaporated under reduced pressure to provide triisopropylsilyl 9-(tetrazol-2-yl)-9-deoxyclavulanate (190 mg) as a colourless gum. $v_{max}$ (CHCl$_3$) 1800, 1730, 1700 cm$^{-1}$; δ (CDCl$_3$) 0.9-1.6 (21H, m, (Pr$^i$)$_3$), 3.10 (1H, d, J 17 Hz, 6β-CH), 3.54 (1H, dd, J 17 Hz, 6α-CH), 4.9-5.2 (2H, m, 3-CH and 8-CH), 5.3-5.5 (2H, m, 9-CH$_2$), 5.79 (1H, d, J 2.5 Hz, 5-CH), 8.47 (1H, s, tetrazol-H).

EXAMPLE 31

Lithium 9-(tetrazol-2-yl)-9-deoxyclavulanate

Triisopropylsilyl 9-(tetrazol-2-yl)-9-deoxyclavulanate (90 mg) was dissolved in distilled tetrahydofuran (9 ml), ice cooled and treated with 1N aqueous hydrochloric acid (1 ml). The solution was stirred 25 minutes at 0°-5° C. and saturated brine (20 ml) added. The resulting mixture was extracted with ethyl acetate (2×30 ml) and the ethyl acetate dried over MgSO$_4$ and evaporated. The residue was taken up in distilled tetrahydrofuran (5 ml) and water (5 ml) and the solution brought to pH 7 with 1N LiOH solution. A further 10 ml water was added and the mixture washed with ethyl acetate (2×20 ml) and freeze dried to provide lithium 9-(tetrazol-2-yl)-9-deoxyclavulanate (51 mg) as a pale yellow solid identical with the product of example 7.

EXAMPLE 32

Benzyl 9-(5-tert.butyltetrazol-1-yl)deoxyclavulanate

A solution of benzyl 9-aminodeoxyclavulanate in ethyl acetate was reacted with pivaloyl chloride to afford the pivalamide (0.36 g). The pivalamide (0.256 g) in dry dichloromethane (10 ml) was cooled to 0° C. Pyridine (0.11 ml) and 12.5% COCl$_2$ in toluene (1.08 ml) were added, stirred for 6 hours, then evaporated to dryness. The residue was taken up in dry dichloromethane and stirred at 0° C. Tetramethylguanidinium azide (0.286 g) was added, the reaction mixture was stirred for one hour at ambient temperature, washed with 0.5M aqueous HCl and dried over MgSO$_4$. The desiccant was filtered off and the filtrate evaporated. The residue was subjected to column chromatography on silica gel using 2:1 ethyl acetate-cyclohexane as eluent. Fractions containing the desired product were combined and evaporated, to yield the title product (0.16 g); Ir (film) 1800 (β-lactam C=O) 1745 (ester) 1695 (C=C).

EXAMPLE 33

Potassium 9-(5-tert.butyltetrazol-1-yl)deoxyclavulanate

The benzyl ester (0.237 g) in redistilled tetrahydrofuran (20 ml) was hydrogenated over 10% palladised charcoal (monitored by tlc). After 45 minutes the catalyst was filtered off, the filtrate cooled to 0° C. and diluted with water (40 ml). The solution was adjusted to pH 7 with 1M potassiumhydroxide solution and evaporated to dryness to yield 0.2 g of crude potassium salt. The product was chromatographed on silica gel using 2:1:1 butanol-ethanol-water as elution solvent. Fractions containing the desired product were combined and evaporated, to yield 0.16 g of pure product; nmr(D$_2$O)δ:1.46(9H, s, tert Bu) 3.07(1H, d, J 17 Hz, 6-β-CH) 3.56(1H, dd, J 3 and 17 Hz, 6-α-CH) ca 4.95 (2H, m, 3-CH and 8-CH) 5.17–5.37(2H, m, 9-CH$_2$) and 5.75(1H, d, J 3 Hz, 5-CH).

EXAMPLE 34

Benzyl 9-(5-formamidotetrazolyl)deoxyclavulanate (i) 5-Formamidotetrazole

5-Aminotetrazole monohydrate (10 g) was heated under reflux in anhydrous formic acid for 48 hours. The mixture was cooled, and the 5-formamidotetrazole filtered off, washed with formic acid, ether, and dried in vacuo, to yield 8.3 g of the tetrazole: IR(nujol mull) C=O at 1680 cm$^{-1}$.

(ii) Benzyl 9-(5-formamidotetrazolyl)deoxyclavulanate

Following the procedure of Example II, the title compound was obtained with an Rf (in 1:1 ethyl acetate-cyclohexane) of about 0.4; above triphenylphosphine oxide: IR (liquid film) 1800 (β-lactam C=O), 1745 (ester C=O) and 1695 cm$^{-1}$ (C=C and amide C=O).

EXAMPLE 35

Lithium 9-(5-formamidotetrazolyl)deoxyclavulanate

The product from Example 34 (0.45 g) in tetrahydrofuran was hydrogenated over 10% palladised charcoal (0.2 g). When the reaction was complete, the catalyst was removed by filtration, water added and the mixture titrated to pH 7.0 with 1M LiOH. The solution was evaporated to dryness, triturated with acetone and the product collected by filtration and dried: IR (nujol) 1770 (β-lactam C=O) 1700 (broad, C=C and amide C=O) 1603 and 1575 cm$^{-1}$ (CO$_2$$^-$): Ir (KBr disc) 3400 (NH, H$_2$O) 1780 (β-lactam C=O) 1700 (C=C and amide C=O) 1610 and 1580 cm$^{-1}$ (CO$_2$$^-$).

DEMONSTRATION OF EFFECTIVENESS

In a standard MIC test the following data were obtained for the synergistic activity of tetrazolyl derivatives with amoxycillin.

| Amoxycillin and compound of example number | dose of compound of this invention | MIC μg/ml amoxycillin | | |
|---|---|---|---|---|
| | | St. Aureus Russell | K. aerogenes E70 | E. coli JT39 |
| 7 | 5.0 μg/ml | 0.02 | 0.4 | 2.0 |
| | 1.0 μg/ml | 0.6 | 3.1 | 4.0 |
| 10 | 5.0 μg/ml | 0.04 | 0.4 | — |
| | 1.0 μg/ml | 0.3 | 3.1 | 4.0 |
| 12 | 5.0 μg/ml | 0.08 | 1.5 | ≦0.5 |
| | 1.0 μg/ml | 0.3 | 3.1 | 4.0 |
| 35 | 5.0 μg/ml | 0.16 | 1.6 | 4.0 |
| | 1.0 μg/ml | 0.6 | 6.2 | 8.0 |
| 14 | 5.0 μg/ml | 0.8 | 3.1 | 0.5 |
| | 1.0 μg/ml | 3.1 | 6.2 | 8.0 |
| 15 | 5.0 μg/ml | 0.3 | 1.6 | 4.0 |
| | 1.0 μg/ml | 2.5 | 6.2 | 31.2 |
| 18 | 5.0 μg/ml | 0.08 | 0.4 | 2.0 |
| | 1.0 μg/ml | 0.6 | 3.1 | 4.0 |
| 27 | 5.0 μg/ml | — | 100 | 62.5 |
| | 1.0 μg/ml | 0.4 | >100 | 500 |
| 25 | 5.0 μg/ml | 0.16 | 0.8 | — |
| | 1.0 μg/ml | 0.6 | 3.1 | 8.0 |
| amoxycillin alone | | 500 | 1000 | 2000 |

In a standard MIC test the following antibacterial activities were obtained.

| Compound of example No. | St. aureus Russell | K. aerogenes E70 | E.coli JT39 |
|---|---|---|---|
| 7 | 16.0 | 16.0 | 16.0 |
| 10 | 8.0 | 31.2 | 8.0 |
| 12 | 16.0 | 31.2 | 16.0 |
| 35 | 16.0 | 62.5 | 31.2 |
| 14 | 8.0 | 31.2 | 8.0 |
| 15 | 16.0 | 31.2 | 16.0 |
| 18 | 16.0 | 62.5 | 16.0 |
| 27 | 4.0 | >500 | 125 |
| 25 | 16.0 | 62.5 | 8.0 |

I claim:

1. A compound of the formula (II) or a pharmaceutically acceptable salt or non-toxic in-vivo hydrolyzable ester thereof:

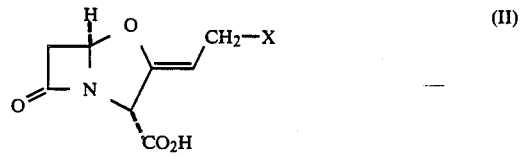

wherein X is tetrazolyl attached via a nitrogen atom, said tetrazolyl moiety being unsubstituted or substituted by a carboxyl salt, an in-vivo hydrolyzable carboxyl ester of the formula (b), (c), (d) or (e):

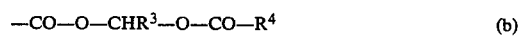  —CO—O—CHR$^3$—O—CO—R$^4$ (b)

  —CO—O—R$^5$—NR$^6$R$^7$ (c)

  CO—OA$^1$ (d) or

  CO—O—CHA$^2$A$^3$ (e)

wherein R$^3$ is hydrogen, methyl or phenyl; R$^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or R$^3$ and R$^4$ are together with the —O—CO— moiety to which they are attached form a phthalidyl or 3,4-dimethoxyphthalidyl moiety; R$^5$ is methylene or ethylene; R$^6$ and R$^7$ are each methyl or ethyl; A$^1$ is alkyl of 1 to 6 carbon atoms unsubstituted or substituted by an alkoxy of 1 to 7 carbon atoms; A$^2$ is alkenyl of 2 to 5 carbon atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and A$^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

—(CO)$_n$—NR$^1$R$^2$     (a)

wherein n is zero or one; R$^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and R$^2$ is hydrogen, alkyl of 1 to 6 carbon atoms, or alkanoyl of 1 to 6 carbon atoms, or R$^1$ and R$^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when R$^1$ or R$^2$ is other than methyl, said R$^1$ or R$^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or R$^1$ and R$^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl.

2. A compound according to claim 1 wherein X is a group of the sub-formula (i):

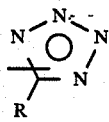
(i)

wherein R is hydrogen, a carboxyl salt, an in-vivo hydrolyzable carboxy ester of the formula (b), (c), (d) or (e):

—CO—O—CHR$^3$—O—CO—R$^4$     (b)

—CO—O—R$^5$—NR$^6$R$^7$     (c)

CO—OA$^1$     (d) or

CO—O—CHA$^2$A$^3$     (e)

wherein R$^3$ is hydrogen, methyl or phenyl; R$^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or R$^3$ and R$^4$ are together with the CH—O—CO— moiety to which they are attached form a phthalidyl or 3,4-dimethoxyphthalidyl moiety; R$^5$ is methylene or ethylene; R$^6$ and R$^7$ are each methyl or ethyl; A$^1$ is alkyl of 1 to 6 carbo atoms unsubstituted or substituted by an alkoxy of 1 to 7 carbon atoms; A$^2$ is alkenyl of 2 to 5 carbon atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and A$^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

—(CO)$_n$—NR$^1$R$^2$     (a)

wherein n is zero or one; R$^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and R$^2$ is hydrogen, alkyl of 1 to 6 carbon atoms, or alkanoyl of 1 to 6 carbon atoms, or R$^1$ and R$^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when R$^1$ or R$^2$ is other than methyl, said R$^1$ or R$^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or R$^1$ and R$^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl.

3. A compound according to claim 2 wherein R is hydrogen, alkoxy of 1 to 6 carbon atoms, alkyl of 1 to 6 carbon atoms, alkenyl of 2 to 6 carbon atoms or aryl unsubstituted or substituted by hydroxy, halo, aryl, carboxy, alkanoyl of 1 to 6 carbon atoms alkanoyloxy of 1 to 6 carbon atoms, alkoxy of 1 to 6 carbon atoms, alkoxycarbonyl of 1 to 6 carbon atoms, arylalkoxy of 1 to 6 carbon atoms in the alkyl moiety, arylcarbonyl, alkylthio of 1 to 6 carbon atoms in the alkyl moiety, arylthio, amino, azido, mono-alkenylamino of 1 to 6 carbon atoms in the alkyl moiety or di-alkylamino of 1 to 6 carbon atoms in each alkyl moiety; azido, isocyano, cyano, nitro, bromo, chloro; or is a group of the sub-formula (aa):

—NR$^1$R$^2$     (aa)

wherein R$^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and R$^2$ is hydrogen, alkyl of 1 to 6 carbon atoms, or alkanoyl of 1 to 6 carbon atoms, or R$^1$ or R$^2$ is methyl substituted by carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when $R^1$ and $R^2$ is other than methyl, said $R^1$ or $R^2$ moiety is substituted by hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl.

4. A compound according to claim 1 selected from the group consisting of:
sodium 9-(5-acetamidotetrazolyl)deoxyclavulante,
sodium 9-(5-ethoxycarbonyltetrazol-1-yl)deoxyclavulanate,
disodium 9-(5-carboxylatotetrazol-1-yl)deoxyclavulanate,
dipotassium 9-(5-carboxylatotetrazol-1-yl)deoxyclavulanate,
sodium 9-(tetrazol-1-yl)deoxyclavulanate,
potassium 9-(tetrazol-1-yl)deoxyclavulanate,
potassium 9-(5-methyltetrazol-1-yl)deoxyclavulanate,
potassium 9-(5-phenyltetrazol-1-yl)deoxyclavulanate,
potassium 9-(5-tert-butyltetrazol-1-yl)deoxyclavulanate, and
methoxymethyl 9-(tetrazol-2-yl)deoxyclavulanate.

5. A compound according to claim 1 in the form of a non-toxic in vivo hydrolyzable ester.

6. A compound according to claim 1 in the form of a pharmaceutically acceptable salt wherein said salt is ametal salt, alkali metal salt, alkaline earth metal salt, an ammonium salt, or a procaine, dibenzylammonium, N,N-dibenzylethylenediammonium, 1-ephanammonium, N-ethylpiperidinium, N-benzyl-beta-phenethylammonium, dehydroabiethylammonium or N,N-disdehydroabietylammonium salt.

7. A compound according to claim 1 in the form of a pharmaceutically acceptable salt wherein said salt is the sodium, potassium, aluminum, calcium, magnesium, ammonium, triethylammonium, 2-hydroxyethylammonium, bis-(2-hydroxyethyl)ammonium, tri-(2-hydroxyethyl)ammonium, dicyclohexlyammonium, dibenzylammonium, N,N-dibenzylethylene-diammonium, 1-ephenammonium, N-ethylpiperidinium, N-benzyl-beta-phenethyl-ammonium, dehydroabietylammonium or N,N-bisdehydroabietyl-ammonium salt.

8. A non-pharmaceutically acceptable salt of a compound of the formula (II):

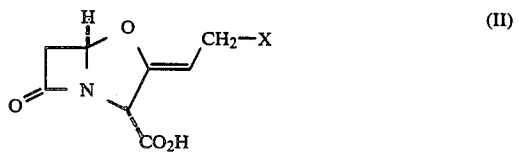

(II)

wherein X is tetrazolyl attached via a nitrogen atom, said tetrazolyl moiety being unsubstituted or substituted by a carboxyl salt, an in-vivo hydrolyzable carboxyl ester of the formula (b), (c), (d) or (e):

$$-CO-O-CHR^3-O-CO-R^4 \qquad (b)$$

$$-CO-O-R^5-NR^6R^7 \qquad (c)$$

$$CO-OA^1 \qquad (d)$$

or $$CO-O-CHA^2A^3 \qquad (e)$$

wherein $R^3$ is hydrogen, methyl or phenyl; $R^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or $R^3$ and $R^4$ are together with the CH—O—CO— moiety to which they are attached form a phthalidyl or 3,4-dimethoxyphthalidyl moiety; $R^5$ is methylene or ethylene; $R^6$ and $R^7$ are each methyl or ethyl; $A^1$ is alkyl of 1 to 6 carbon atoms unsubstituted or substituted by an alkoxy of 1 to 7 carbon atoms; $A^2$ is alkenyl of 2 to 5 carbo atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and $A^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

$$-(CO)_n-NR^1R^2 \qquad (a)$$

wherein n is zero or one; $R^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and $R^2$ is hydrogen, alkyl of 1 to 6 carbon atoms, or alkanoyl of 1 to 6 carbon atoms, or $R^1$ and $R^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when $R^1$ or $R^2$ is other than methyl, said $R^1$ or $R^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring wherein the nitrogen atom is the only heteroatom, and wherein aryl as used herein is phenyl, pyrrolyl, thienyl, indolyl, benzofuryl, or thianaphthyl.

9. A salt according to claim 8 selected from the group consisting of:
lithium 9-(tetrazol-2-yl)deoxyclavulanate,
lithium 9-(5-aminotetrazolyl)deoxyclavulanate,
lithium 9-(5-ethoxycarbonyltetrazol-1-yl)deoxyclavulanate and
lithium 9-(tetrazol-1-yl)deoxyclavulanate.

10. A pharmaceutical composition useful for treating bacterial infections in humans and animals which comprises an antibacterially effective amount or a betalactamase inhibitory amount of a compound of the formula (II):

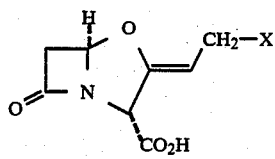

or a pharmaceutically acceptable salt or pharmaceutically acceptable in-vivo hydrolyzable ester thereof, wherein X is a tetrazolyl attached via a nitrogen atom, said tetrazolyl moiety being unsubstituted or substituted by a carboxyl salt, an in-vivo hydrolyzable carboxyl ester of the formula (b), (c), (d) or (e):

—CO—O—CHR$^3$—O—CO—R$^4$ (b)

—CO—O—R$^5$—NR$^6$R$^7$ (c)

CO—OA$^1$ (d) or

CO—O—CHA$^2$A$^3$ (e)

wherein R$^3$ is hydrogen, methyl or phenyl; R$^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or R$^3$ and R$^4$ are together with the CH—O—CO— moiety to which they are attached form a phthalidyl or 3,4-dimethoxyphthalidyl moiety; R$^5$ is methylene or ethylene; R$^6$ and R$^7$ are each methyl or ethyl; A$^1$ is alkyl of 1 to 6 carbon atoms unsubstituted or substituted by an alkoxy of 1 to 7 carbon atoms; A$^2$ is alkenyl of 2 to 5 carbon atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and A$^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

—(CO)$_n$—NR$^1$R$^2$ (a)

wherein n is zero or one; R$^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and R$^2$ is hydrogen, alkyl of 1 to 6 carbon atoms, or alkanoyl of 1 to 6 carbon atoms, or R$^1$ and R$^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when R$^1$ or R$^2$ is other than methyl, said R$^1$ or R$^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or R$^1$ and R$^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl, in combination with a pharmaceutically acceptable carrier.

11. A composition according to claim 10 wherein X is a group of sub-formula (i):

wherein R is hydrogen, a carboxyl salt, an in-vivo hydrolyzable carboxy ester of the formula (b), (c), (d) or (e):

—CO—O—CHR$^3$—O—CO—R$^4$ (b)

—CO—O—R$^5$—NR$^6$R$^7$ (c)

CO—OA$^1$ (d) or

CO—O—CHA$^2$A$^3$ (e)

wherein R$^3$ is hydrogen, methyl or phenyl; R$^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or R$^3$ and R$^4$ are together with the CH—O—CO— moiety to which they are attached form a phthalidyl or 3,4-dimethoxyphthalidyl moiety; R$^5$ is methylene or ethylene; R$^6$ and R$^7$ are each methyl or ethyl; A$^1$ is alkyl of 1 to 6 carbon atoms unsubstituted or substituted by an alkoxy of 1 to 7 carbon atoms; A$^2$ is alkenyl of 2 to 5 carbon atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and A$^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

—(CO)$_n$—NR$^1$R$^2$ (a)

wherein n is zero or one; R$^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and R$^2$ is hydrogen, alkyl of 1 to 6 carbon atoms, or alkanoyl of 1 to 6 carbon atoms, or R$^1$ and R$^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when R$^1$ or R$^2$ is other than methyl, said R$^1$ or R$^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl.

12. A composition according to claim 10 wherein R is hydrogen, alkoxy of 1 to 6 carbon atoms, alkyl of 1 to 6 carbon atoms, alkenyl of 2 to 6 carbon atoms or aryl unsubstituted or substituted by hydroxy, halo, aryl, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms, arylalkoxy of 1 to 6 carbon atoms in the alkyl moiety, arylcarbonyl, alkylthio of 1 to 6 carbon atoms in the alkyl moiety, arylthio, amino, azido, mono-alkenylamino of 1 to 6 carbon atoms in the alkyl moiety or di-alkylamino of 1 to 6 carbon atoms in each alkyl moiety; azido, isocyano, cyano, nitro, bromo, chloro; or is a group of the sub-formula (aa):

—NR$^1$R$^2$ (aa)

wherein $R^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and $R^2$ is hydrogen, alkyl of 1 to 6 carbon atoms, or alkanoyl of 1 to 6 carbon atoms, or $R^1$ or $R^2$ is methyl substituted by carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when $R^1$ and $R^2$ is other than methyl, said $R^1$ or $R^2$ moiety is substituted by hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl.

13. A composition according to claim 10 wherein the compound is selected from the group consisting of:
sodium 9-(5-acetamidotetrazolyl)deoxyclavulanate,
sodium 9-(5-ethoxycarbonyltetrazol-1-yl)deoxyclavulanate,
disodium 9-(5-carboxylatotetrazol-1-yl)deoxyclavulanate,
dipotassium 9-(5-carboxylatotetrazol-1-yl)deoxyclavulanate,
sodium 9-(tetrazol-1-yl)deoxyclavulanate,
potassium 9-(tetrazol-1-yl)deoxyclavulanate,
potassium 9-(5-methyltetrazol-1-yl)deoxyclavulanate,
potassium 9-(5-phenyltetrazol-1-yl)deoxyclavulanate,
potassium 9-(5-tert-butyltetrazol-1-yl)deoxyclavulanate, and
methoxymethyl 9-(tetrazol-2-yl)deoxyclavulanate.

14. A composition according to claim 10 wherein the compound is in the form of a non-toxic in vivo hydrolyzable ester.

15. A method of treating bacterial infections in humans and animals which comprises administering to a human or animal in need thereof an antibacterially effective amount of a compound of the formula (II):

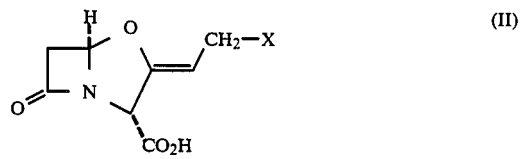

or a pharmaceutically acceptable salt or pharmaceutically acceptable in-vivo hydrolyzable ester thereof, wherein X is a terazolyl attached via a nitrogen atom, said tetrazolyl moiety being unsubstituted or substituted by a carboxyl salt, an in-vivo hydrolyzable carboxyl ester of the formula (b), (c), (d) or (e):

—CO—O—CHR$^3$—O—CO—R$^4$ (b)

—CO—O—R$^5$—NR$^6$R$^7$ (c)

CO—OA$^1$ (d) or

CO—O—CHA$^2$A$^3$ (e)

wherein $R^3$ is hydrogen, methyl or phenyl; $R^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or $R^3$ and $R^4$ are together with the CH—O—CO— moiety to which they are attached form a phthalidyl or 3,4-dimethoxyphthalidyl moiety; $R^5$ is methylene or ethylene; $R^6$ and $R^7$ are each methyl or ethyl; $A^1$ is alkyl of 1 to 6 carbon atoms unsubstituted or substituted by an alkoxy of 1 to 7 carbon atoms; $A^2$ is alkenyl of 2 to 5 carbon atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and $A^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

—(CO)$_n$—NR$^1$R$^2$ (a)

wherein n is zero or one; $R^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and $R^2$ is hydrogen, alkyl of 1 to 6 carbon atoms, or alkanoyl of 1 to 6 carbon atoms, or $R^1$ and $R^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when $R^1$ or $R^2$ is other than methyl, said $R^1$ or $R^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, thianaphthyl, in combination with a pharmaceutically acceptable carrier.

16. A method according to claim 15 wherein X is a group of the sub-formula (i):

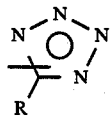
(i)

wherein R is hydrogen, a carboxyl salt, an in-vivo hydrolyzable carboxy ester of the formula (b), (c), (d) or (e):

(b)

(c)

(d) or

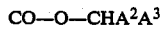
(e)

wherein $R^3$ is hydrogen, methyl or phenyl; $R^4$ is alkyl of 1 to 6 carbon atoms, phenyl, phenylalkyl of 1 to 3 carbon atoms in the alkyl moiety, alkoxy of 1 to 6 carbon atoms, phenoxy or phenylalkoxy of 1 to 3 carbon atoms in the alkyl moiety; or $R^3$ and $R^4$ are together with the CH—O—CO— moiety to which they are attached form a phthalidyl or 3,4-dimethoxyphthalidyl moiety; $R^5$ is methylene or ethylene; $R^6$ and $R^7$ are each methyl or ethyl; $A^1$ is alkyl of 1 to 6 carbon atoms unsubstituted or substituted by an alkoxy of 1 to 7 carbon atoms; $A^2$ is alkenyl of 2 to 5 carbon atoms unsubstituted or substituted by a phenyl moiety; phenyl unsubstituted or substituted by a fluoro, chloro, bromo, nitro, alkyl of 1 to 4 carbon atoms or alkoxy of 1 to 4 carbon atoms; and $A^3$ is hydrogen, alkyl of 1 to 4 carbon atoms or phenyl unsubstituted or substituted by a fluoro, chloro, bromo, nitro, alkyl of 1 to 4 carbon atoms or alkoxy of 1 to 4 carbon atoms; or by a group of the sub-formula (a):

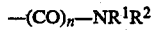
(a)

wherein n is zero or one; $R^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and $R^2$ is hydrogen, alkyl of 1 to 6 carbon atoms, or alkanoyl of 1 to 6 carbon atoms, or $R^1$ and $R^2$ are methyl substituted by a carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when $R^1$ or $R^2$ is other than methyl, said $R^1$ or $R^2$ moiety is substituted by a hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring.

17. A method according to claim 15 wherein R is hydrogen, alkoxy of 1 to 6 carbon atoms, alkyl of 1 to 6 carbon atoms, alkenyl of 2 to 6 carbon atoms or aryl unsubstituted or substituted by hydroxy, halo, aryl, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms, arylalkoxy of 1 to 6 carbon atoms in the alkyl moiety, arylcarbonyl, alkylthio of 1 to 6 carbon atoms in the alkyl moiety, arylthio, amino, azido, mono-alkenylamino of 1 to 6 carbon atoms in the alkyl moiety or di-alkylamino of 1 to 6 carbon atoms in each alkyl moiety; azido, isocyano, cyano, nitro, bromo, chloro; or is a group of the sub-formula (aa):

(aa)

wherein $R^1$ is hydrogen, alkyl of 1 to 6 carbon atoms, alkanoyl of 1 to 6 carbon atoms or arylcarbonyl unsubstituted or substituted by one or more hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, aralkoxy of 1 to 10 carbon atoms in the alkoxy moiety, arylcarbonyl, alkylthio of 1 to 6 carbon atoms in the alkyl moiety, arylthio, amino, alkylamino of 1 to 6 carbon atoms in the alkyl moiety or di-alkylamino of 1 to 6 carbon atoms in each alkyl moiety; and $R^2$ is hydrogen, alkyl of 1 to 6 carbon atoms, or alkanoyl of 1 to 6 carbon atoms, or $R^1$ or $R^2$ is methyl substituted by carboxy, alkanoyl of 1 to 6 carbon atoms, alkanoyloxy of 1 to 6 carbon atoms, alkoxycarbonyl of 1 to 6 carbon atoms or arylcarbonyl and the other is as above defined; or when $R^1$ and $R^2$ is other than methyl, said $R^1$ or $R^2$ moiety is substituted by hydroxy, halo, carboxy, alkanoyl of 1 to 6 carbon atoms, alkanoyloxy of 1 to 6 carbon atoms, alkoxy of 1 to 6 carbon atoms, alkoxycarbonyl of 1 to 6 carbon atoms in the alkoxy moiety, arylalkoxy of 1 to 6 carbon atoms in the alkoxy moiety, arylcarbonyl, alkylthio of 1 to 6 carbon atoms, arylthio, amino, alkylamino of 1 to 6 carbon atoms or di-alkylamino of 1 to 6 carbon atoms; or $R^1$ and $R^2$ are joined to form with the nitrogen atom to which they are attached, a 4-, 5- or 6-membered ring wherein the nitrogen atom is the only heteroatom, and wherein aryl as used herein is phenyl, pyrrolyl, furyl, thienyl, indolyl, benzofuryl, or thianaphthyl.

18. A method according to claim 15 wherein the compound is selected from the group consisting of:
sodium 9-(5-acetamidotetrazolyl)deoxyclavulanate,
sodium 9-(5-ethoxycarbonyltetrazol-1-yl)deoxyclavulanate,
disodium 9-(5-carboxylatotetrazol-1-yl)deoxyclavulanate,
dipotassium 9-(5-carboxylatotetrazol-1-yl)deoxyclavulanate,
sodium 9-(tetrazol-1-yl)deoxyclavulanate,
potassium 9-(tetrazol-1-yl)deoxuclavulanate,
potassium 9-(5-methyltetrazol-1-yl)deoxyclavulanate,
potassium 9-(5-phenyltetrazol-1-yl)deoxyclavulanate,
potassium 9-(5-tert-butyltetrazol-1-yl)deoxyclavulanate, and
methoxymethyl 9-(tetrazol-2-yl)deoxyclavulanate.

19. A method according to claim 15 wherein the compound is in the form of a non-toxic in vivo hydrolyzable ester.

* * * * *